United States Patent [19]

Franz et al.

[11] 4,167,417
[45] Sep. 11, 1979

[54] FLUORESCENT INORGANIC PIGMENT

[75] Inventors: Karl Franz, Barsinghausen; Wolfgang Jäger, Rehburg, both of Fed. Rep. of Germany

[73] Assignee: Riedel-de Haen Aktiengesellschaft, Seelze, Fed. Rep. of Germany

[21] Appl. No.: 917,584

[22] Filed: Jun. 21, 1978

[30] Foreign Application Priority Data

Jun. 23, 1977 [DE] Fed. Rep. of Germany ....... 2728266

[51] Int. Cl.$^2$ .................. C09K 3/00; C09K 11/16; C09K 11/20
[52] U.S. Cl. ........................ 106/35; 32/8.15; 252/301.4 R; 252/301.4 F
[58] Field of Search .................. 106/35; 252/301.4 R, 252/301.4 F; 32/8.15

[56] References Cited

U.S. PATENT DOCUMENTS

| | | | |
|---|---|---|---|
| 2,049,765 | 9/1936 | Fischer | 252/301.4 F |
| 2,171,145 | 8/1939 | Leverenz | 252/301.4 F |
| 2,895,050 | 7/1959 | Lee et al. | 252/301.4 F |

FOREIGN PATENT DOCUMENTS

| | | | |
|---|---|---|---|
| 2307864 | 11/1976 | France | 252/301.4 R |
| 134104 | 12/1974 | Japan . | |

OTHER PUBLICATIONS

German Offenlegungsschrift, 23 57 811, Sep. 18, 1973.

*Primary Examiner*—Theodore Morris
*Attorney, Agent, or Firm*—Curtis, Morris & Safford

[57] ABSTRACT

An inorganic fluorescent pigment for use in artificial teeth is provided and a method for producing the same, the pigment having the formula $$(X\cdot SE + A\cdot Ce + B\cdot Tb + C\cdot Mn)_2O_3\cdot SiO_2$$

wherein
SE is at least one of the elements yttrium, gadolinium and lanthanum,
Ce is cerium,
Tb is terbium,
Mn is manganese,
A is of from 2 to 10 mol percent,
B is of from 2 to 10 mol percent,
C is of from 0.5 to 2.5 mol percent,
X is $100 - (A+B+C)$ mol percent.

In artificial teeth a product is useful with a particle size according to the Coulter-Counter method of
5 percent of from 0.85 to 1.35 μm,
50 percent of from 2.4 to 4.1 μm and
95 percent of from 7.8 to 18.0 μm.

The pigment may be produced by heating a mixture of the SE, Ce— and SiO$_2$ compounds at a temperature of above 1000° C., grinding the resulting product, mixing it with Tb and Mn compounds and heating it again at a temperature of above 1000° C. in a reducing atmosphere. After grinding the resulting product, the portion having the desired particle size may be selected.

4 Claims, No Drawings

FLUORESCENT INORGANIC PIGMENT

The invention relates to a fluorescent inorganic pigment, to a process for producing the same and to its use as fluorescent additive to artificial teeth.

When exposed to ultraviolet light, natural teeth exhibit a yellowish-white fluorescence. Dental preparations and artificial teeth, which have comparable optical properties, are of great interest in dentistry.

For this reason, uranium compounds have been added to the above products in recent years. These compounds, however, have the disadvantage of being radioactive. Since this radiation may cause injuries to health, attempts have been made for a long time to find a luminescent pigment free from radioactivity which should be suitable for this application field.

A pigment of this type should fulfil mainly the following requirements: It must exhibit a white-yellow fluorescence upon the action of mainly long-wave ultraviolet radiation. The turbidity and color of the dental preparations should not change when adding the substances concerned. The pigment should not change or change only slightly with regard to its turbidity and luminescent properties when incorporated into the artificial tooth composition.

The present invention consequently was confronted with the problem of providing a fluorescent inorganic pigment fulfilling the above requirements.

It has now been found that these requirements are fulfilled by an inorganic pigment which has the following composition:

$$(X.SE + A.Ce + B.Tb + C.Mn)_2O_3.SiO_2$$

in which the symbols have the following meanings:
SE is at least one of the elements yttrium, gadolinium and lanthanum,
A is 2 to 10 mol percent,
B is 2 to 10 mol percent,
C is 0.5 to 2.5 mol percent,
X is $100-(A+B+C)$ mol percent.

SE may be yttrium, gadolinium or lanthanum or a mixture of these elements, yttrium being preferred. Suitable activators are cerium, terbium and manganese.

Fluorescent substances based on terbium-activated yttrium oxide have been proposed, for example, in Japanese Pat. No. 74-134104. The activation of yttrium aluminum oxide (cf. Japanese Pat. No. 69-082182) and of lanthanum aluminum oxide (cf. German Offenlegungsschrift 23 57 811) with the simultaneous use of cerium and terbium is moreover known. The luminescent pigments obtained may be activated by ultraviolet, electronic or X-radiation to exhibit a green or green-yellow fluorescence. Pigments of the above composition are not suited for use in artificial teeth and dental preparations because of the spectral distribution of the fluorescent radiation.

It has now been found surprisingly that the addition of manganese ions as activator for a pigment of the above type makes it possible to obtain a product which highly meets the demands on a luminescent pigment for use in dental preparations and artificial teeth as regards the proper color when exposed to daylight, the spectral distribution of the fluorescent light, the processability and the profitableness.

The fluorescence of the pigment obtained upon the action of ultraviolet radiation of a wide wave length range depends on the portion of the individual activators and may reach from blue-white to yellow-white.

A compound of the following composition
$(Y_{93.7}Ce_{2.1}Tb_{3.3}Mn_{0.9})_2O_3.SiO_2$
is especially appropriate for use in dental preparations and artificial teeth made from porcelain.

Test of the applicant have shown that the components should not be mixed and heated advantageously for preparing a luminescent pigment of the above type. However, when proceeding in the following manner, there is obtained a product of relatively high luminosity: In a first heating process a mixture of
X mol percent of SE compounds,
A mol percent of cerium compounds and
100 mol percent of $SiO_2$ is heated at at temperature highe than 1000° C., the resulting product is ground and subsequently mixed with
B mol percent of terbium compounds and
C mol percent of manganese compounds, SE, A, B, C and X having the above-indicated meanings, the mixture obtained is heated at a temperature higher than 1000° C. under reducing conditions and subsequently ground on cooling.

As regards the fineness of grinding, a product having the following particle size distribution:
5 percent of from 0.85 to 1.35 μm,
50 percent of from 2.4 to 4.1 μm and
95 percent of from 7.8 to 18.0 μm according to the Coulter-Counter method proved to have the best distribution in the dental preparation and a color effect which is most similar to that of natural teeth. For this reason, the above particle size distribution should be adjusted by sieving after grinding during the preparation of a luminescent pigment for use in dental preparations and artificial teeth.

Other particle size distributions may be more advantageous for different applications.

It has proved advantageous for the preparation of the above pigment to use cerium in the form of a compound containing tetravalent cerium terbium in the form of $Tb_4O_7$ and manganese in the form of a bivalent salt and to carry out the two-stage heating process under reducing conditions. These conditions may be set up, for example, by placing the crucible containing material to be heated into a greater crucible charged with carbon. Under the heating conditions, there is formed a CO atmosphere over the material to be heated having a reducing action.

Even when using the activators cerium, terbium, and manganese in trivalent form, the second heating process should be suitably carried out under reducing conditions, to avoid the incorporation of activators in undesired higher-valent form.

The following example illustrate the invention:

PREPARATION EXAMPLE:

600 g of $Y_2O_3$ are ground with 170 g of $SiO_2$ and 40 g of $Ce(SO_4)_2$ for a period of from half an hour to 2 hours in a ball mill. The mixture obtained is fed to a vessel resistant to temperatures of up to 1300° C., for example, a crucible made from sintered corundum and is subsequently heated in an electric furnace for 4 hours at 1300° C. On cooling, the product is introduced into a ball mill and upon the addition of 35 g of $Tb_4O_7$ and 8 g of $MnSO_4$ it is ground again. The ground material is again fed to a crucible and submitted to a second heating process, for 2 hours, at 1300° C., under reducing conditions. For this purpose the crucible containing the material to be heated is placed into a greater crucible and the interspace between both crucibles is filled with carbon.

Upon cooling, the product is ground in a ball mill and thereafter a fraction, which has the following particle size distribution according to the Coulter-Counter method, is separated by an aspirator:

5 percent of from 0.85 to 1.35 μm,
50 percent of from 2.4 to 4.1 μm and
95 percent of from 7.8 to 18.0 μm When the product obtained is used in artificial teeth, there is obtained a dental replacement, which does not differ from natural teeth as regards the optical behavior in visible and in ultraviolet light.

What is claimed is:

1. Fluorescent inorganic pigment having the following composition

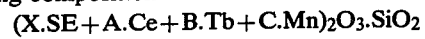

in which the symbols have the following meaning:
SE is at least one of the elements yttrium, gadolinium and lanthanum,
A is of from 2 to 10 mol percent,
B is of from 2 to 10 mol percent,
C is of from 0.5 to 2.5 mol percent,
X is $100-(A+B+C)$ mol percent.

2. Process for the preparation of a fluorescent inorganic pigment as claimed in claim 1, which comprises heating in a first phase a mixture of
X mol percent of SE compounds,
A mol percent of cerium compounds and
100 mol percent of $SiO_2$ at a temperature of above 1000° C., subsequently grinding the resulting product and mixing it with B mol percent of terbium compounds and C mol percent of manganese compounds, SE, A, B, C and X having the meaning given above, heating the mixture obtained at a temperature of above 1000° C. in a reducing atmosphere and grinding it after cooling.

3. Process as claimed in claim 2, which comprises adjusting the particle size distribution of the product after grinding by sieving according to the Coulter-Clounter method as follows:
5 percent of from 0.85 to 1.35 μm,
50 percent of from 2.4 to 4.1 μm and
95 percent of from 7.8 to 18.0 μm.

4. Method of using a fluorescent inorganic pigment as claimed in claim 1 with A being 2.1 mol percent, B 3.3 mol percent and C 0.9 mol percent and having a particle size distribution according to the Coulter-Counter method of
5 percent of from 0.85 to 1.35 μm,
50 percent of from 2.4 to 4.1 μm and
95 percent of from 7.8 to 18.0 μm as fluorescent additive to dental preparations and artificial teeth.

* * * * *